US009415217B2

(12) United States Patent
Chen

(10) Patent No.: US 9,415,217 B2
(45) Date of Patent: Aug. 16, 2016

(54) WIRELESS ELECTRICAL STIMULATION SYSTEM

(71) Applicant: Eric Ye Chen, St. Louis, MO (US)

(72) Inventor: Eric Ye Chen, St. Louis, MO (US)

(73) Assignee: Eric Ye Chen, St. Louis, MO (US)

( * ) Notice: Subject to any disclaimer, the term of this patent is extended or adjusted under 35 U.S.C. 154(b) by 63 days.

(21) Appl. No.: 14/328,433

(22) Filed: Jul. 10, 2014

(65) Prior Publication Data

US 2016/0008609 A1   Jan. 14, 2016

(51) Int. Cl.
| | | |
|---|---|---|
| *A61N 1/375* | (2006.01) | |
| *A61N 1/36* | (2006.01) | |
| *A61N 1/04* | (2006.01) | |
| A61N 1/372 | (2006.01) | |
| A61N 1/32 | (2006.01) | |

(52) U.S. Cl.
CPC .......... *A61N 1/36014* (2013.01); *A61N 1/0452* (2013.01); *A61N 1/0456* (2013.01); *A61N 1/0492* (2013.01); *A61N 1/37217* (2013.01); A61N 1/048 (2013.01); A61N 1/322 (2013.01); A61N 1/36128 (2013.01); A61N 1/37235 (2013.01); A61N 1/37247 (2013.01)

(58) Field of Classification Search
CPC ........... A61N 1/37235; A61N 1/37247; A61N 1/36128; A61N 1/37252; A61N 1/37288; A61N 1/0492; A61N 1/0404
USPC ................................................ 607/48, 59, 60
See application file for complete search history.

(56) References Cited

U.S. PATENT DOCUMENTS

| | | | |
|---|---|---|---|
| 6,445,955 B1 | 9/2002 | Michelson et al. | |
| 7,136,703 B1* | 11/2006 | Cappa | A61N 1/37211 607/30 |
| 2002/0068961 A1* | 6/2002 | Fischer et al. | 607/59 |
| 2002/0183803 A1* | 12/2002 | Fang | A61N 1/025 607/48 |
| 2003/0114898 A1* | 6/2003 | Von Arx et al. | 607/60 |
| 2003/0153958 A1* | 8/2003 | Yamazaki et al. | 607/48 |
| 2004/0015205 A1* | 1/2004 | Whitehurst et al. | 607/48 |
| 2005/0137643 A1* | 6/2005 | Mintchev | A61N 1/36007 607/40 |
| 2006/0247736 A1* | 11/2006 | Roberts | A61N 1/37276 607/60 |
| 2007/0088405 A1* | 4/2007 | Jacobson | 607/59 |
| 2007/0150024 A1* | 6/2007 | Leyde et al. | 607/45 |
| 2007/0173906 A1* | 7/2007 | Yamazaki | 607/60 |
| 2010/0070011 A1* | 3/2010 | Tsumura et al. | 607/142 |
| 2013/0096641 A1 | 4/2013 | Strother et al. | |
| 2013/0253613 A1 | 9/2013 | Salahovic et al. | |
| 2013/0338729 A1 | 12/2013 | Spector | |

FOREIGN PATENT DOCUMENTS

| | | | | |
|---|---|---|---|---|
| WO | WO 2013/106644 | | 7/2013 | A61N 1/00 |

* cited by examiner

*Primary Examiner* — Edward Moran
*Assistant Examiner* — Pamela M Bays
(74) *Attorney, Agent, or Firm* — Harness, Dickey & Pierce, P.L.C.

(57) ABSTRACT

A system and method are provided for a wireless electrical stimulation. The system generally includes at least two electrical stimulation units. Each electrical stimulation unit includes electrodes connected to the unit. The system also includes a transmitter for remotely, wirelessly controlling each of the electrical stimulation units to selectively apply a time-varying electric potential to the electrodes to provide an electrical stimulation to tissue in electrical contact with the electrodes.

23 Claims, 18 Drawing Sheets

WIRELESS ELECTRICAL STIMULATION SYSTEM

FIELD

The present disclosure relates to wireless electrical stimulation systems, such as Transcutaneous Electrical Nerve Stimulation (TENS) and Electrical Muscle Stimulation (EMS) systems.

BACKGROUND

This section provides background information related to the present disclosure which is not necessarily prior art.

Electrical stimulation systems, such as Transcutaneous Electrical Nerve Stimulation (TENS) devices, Electrical Muscle Stimulation (EMS) devices, etc., can provide a stimulating waveform and electrical pulses to muscle groups and or nerve areas of the body, more particularly using electrode pads to deliver electrical pulses to particular areas of human bodies for pain relief.

Conventional electrical stimulation systems typically have a control unit hard-wired to a set of electrodes. Typical tethered control units are inconvenient to use, allow for only one treatment at a time, and provide little information to the user regarding the therapy being delivered. Wireless controls have been proposed, but for the most part they function similarly to the tethered control units.

SUMMARY

This section provides a general summary of the disclosure, and is not a comprehensive disclosure of its full scope or all of its features.

Embodiments of the present disclosure provide wireless electrical stimulation systems. According to a preferred embodiment, the system generally includes at least two electrical stimulation units. Each electrical stimulation unit includes electrodes connected to the unit. The system also includes a transmitter for remotely, wirelessly controlling each of the electrical stimulation units to selectively apply a time-varying electric potential to the electrodes to provide an electrical stimulation to tissue in electrical contact with the electrodes. In some preferred embodiments, a processor may be used to apply the time-varying electric potential to the electrodes to provide the electrical stimulation to tissue in electrical contact with the electrodes.

In some embodiments, the electrodes can be releasably connected to the electrical stimulation unit.

In some embodiments, the transmitter can include a unit selector for selecting one of the at least two electrical stimulation units to control with the transmitter.

In some embodiments, the transmitter can include a display for indicating which of the electrical stimulation units has been selected, and/or other information about the operation of the electrical stimulation units.

In some embodiments, at least some of the electrical stimulation units can have at least two operating modes, each of which applies a time-varying electrical potential to the electrodes in a different pattern. In these embodiments, the transmitter can have a mode selector for selecting one of the at least two operating modes. The transmitter can also include a display for indicating which of the operating modes has been selected.

In some embodiments, at least some of the electrical stimulation units are capable of operating at least two intensities. In these embodiments, the transmitter can have an intensity selector for selecting one of the at least two intensities of operation. The intensity selector can additionally or alternatively include controls for increasing and decreasing intensity. The transmitter can also include a display for indicating the intensity that has been selected. In some embodiments, at least some of the electrical stimulation units are capable of operating for a selectable time period, and the transmitter has a time selector for selecting the time period of operation. The transmitter can also include a display for indicating the selected operating time period.

In some embodiments, the transmitter is a smart phone running an application.

In some embodiments, the electrical stimulation unit is carried on a flexible substrate adapted to be applied on a body surface. In some embodiments, the electrical stimulation unit is carried on an article of clothing (e.g., gloves, socks, slippers, etc.) that can directly contact particular areas of a body surface.

In some embodiments, the transmitter communicates with the electrical stimulation units via a radio frequency (RF) protocol.

In some embodiments, at least some of the electrical stimulation units turn off when communication with the transmitter is interrupted. In some embodiments, at least some of the electrical stimulation units turn off a predetermined time after communication with the transmitter is interrupted.

In some embodiments, at least some of the electrical stimulation units have a power switch and an indicator that indicates when the power is on. The electrical stimulation unit may further include an internal power supply, and an indicator for indicating the status of the internal power supply.

According to another aspect of the present disclosure, a method is provided for operating a plurality of wireless electrical stimulation units on a subject. The method generally includes remotely, wirelessly transmitting operating instructions to each of the plurality of wireless electrical stimulation units on separate channels using a single remote control.

In some embodiments, each of the wireless electrical stimulation units ceases operation within a predetermined period of time losing communication with the remote control.

In some embodiments, the operating instructions include at least one of intensity and duration.

In some embodiments, each of the wireless electrical stimulation units has at least two modes of operation, and wherein the operating instructions include a user selected one of the at least two modes of operation.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Embodiments of the present disclosure provide wireless electrical stimulation systems and operating methods of a plurality of wireless electrical stimulation units on a subject. Thus embodiments of the present disclosure can be used to conveniently control electrode pads to deliver electrical pulses to particular areas of human bodies for nerve and/or muscle stimulation.

Figure 1:
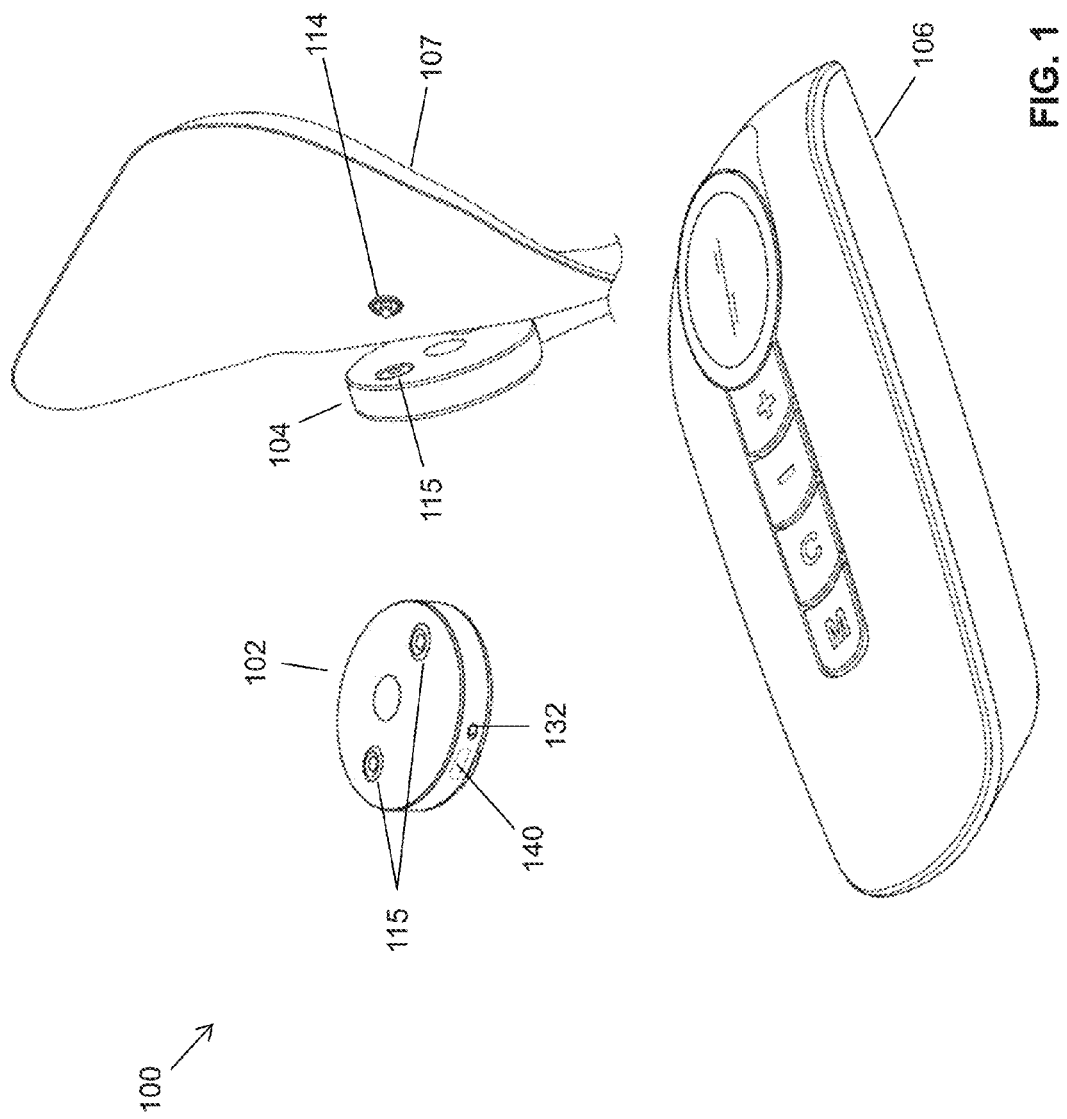
FIG. 1 is a view of an exemplary embodiment of an electrical stimulation system according to the present disclosure.

As shown in FIG. 1, an exemplary embodiment of a wireless electrical stimulation system 100 generally includes at least two electrical stimulation units 102, 104, and a transmitter 106. The transmitter 106 remotely, wirelessly controls each of the electrical stimulation units 102, 104 to deliver electrical pulses to body tissue via electrode pads 107 connected to the electrical stimulation unit. The number of the electrical stimulation units can be as many as desired.

Figure 2:
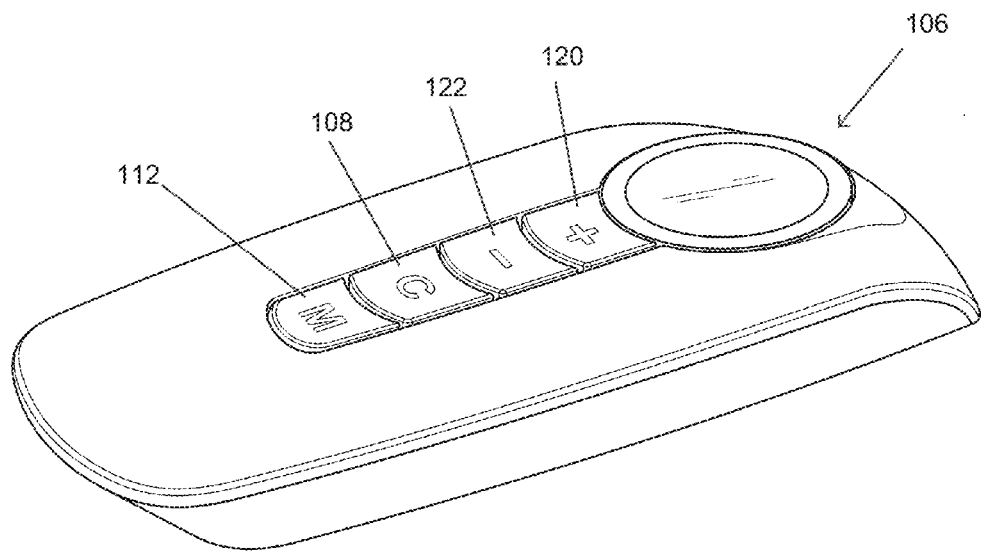
FIG. 2 is a perspective view of a transmitter of the wireless electrical stimulation system.
Figure 3:
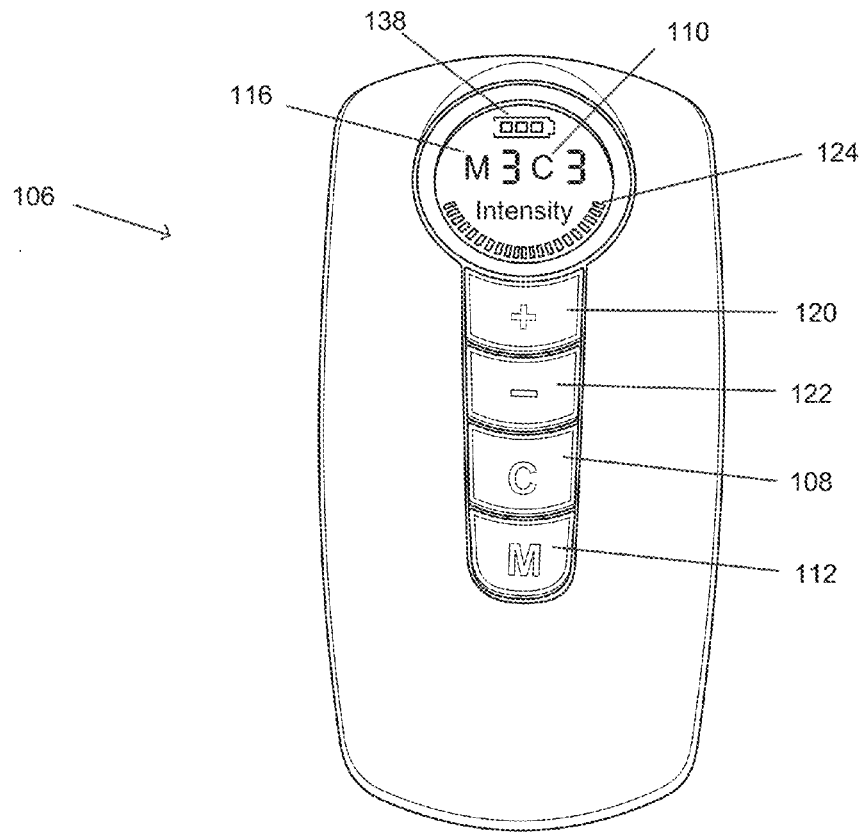
FIG. 3 is a front elevation view of the transmitter.
Figure 4:
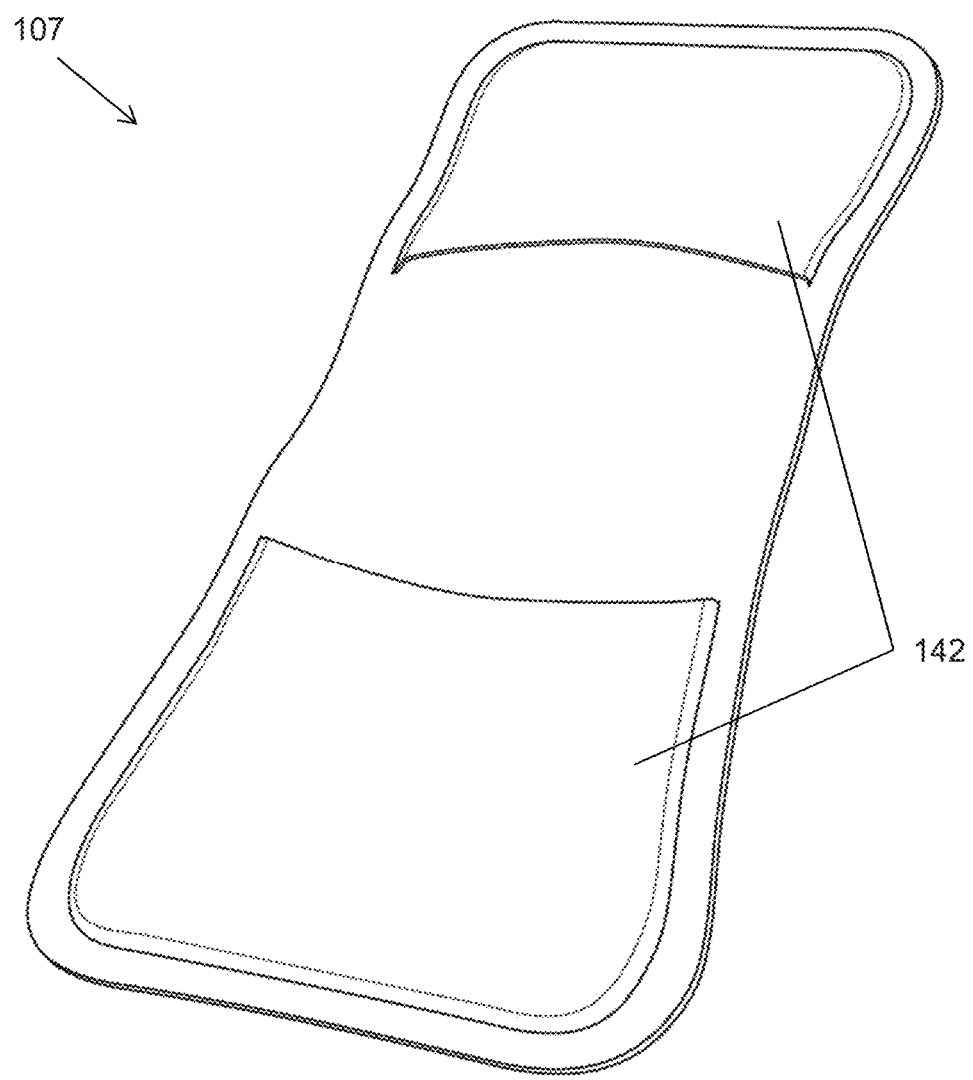
FIG. 4 is a front elevation view of the electrode substrate.
Figure 6:
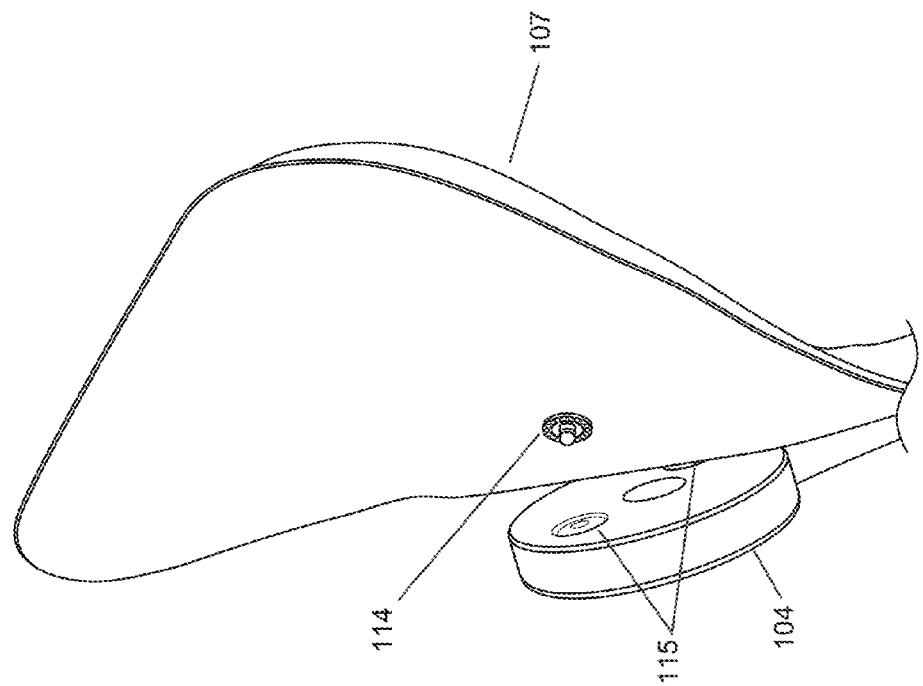
FIGS. 6 and 7 are perspective views illustrating attachment of the electrode substrate of FIGS. 4 and 5 to the electrical stimulation unit.
Figure 5:
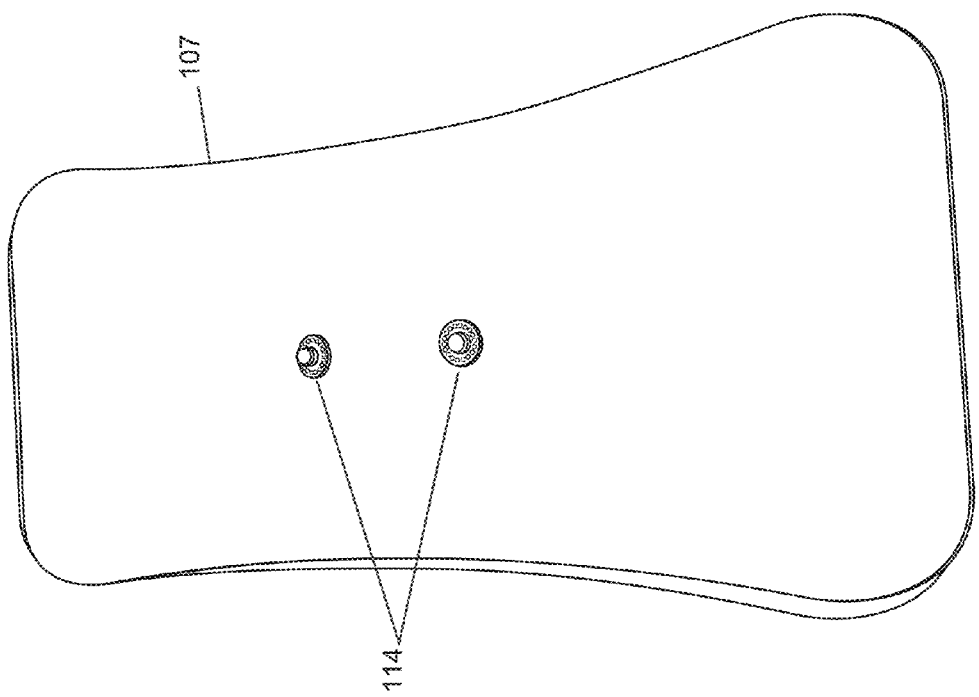
FIG. 5 is a back elevation view of the electrode substrate.

As shown in FIGS. 2-3, the transmitter 106 generally includes a unit selector 108 for selecting one electrical stimulation units to control with the transmitter 106. In this preferred embodiment the unit selector 108 is a single remote control button that allows the user to select a channel to remotely, wirelessly transmit operating instructions to one of the plurality of wireless electrical stimulation units. The unit selector button 108 preferably has a letter "C" on it, indicating to the user that the button 108 controls the channel selection. A user can select different wireless electrical stimulation unit by pressing the button 108, which can cycle through the available channels. In an alternative embodiment, pressing the button 108 switches the transmitter to the channel mode, and the channel can be increased by pressing increase and decrease buttons 120 and 122, described in more detail below.

The transmitter 106 preferably also includes a display 110 for indicating which of the electrical stimulation units has been selected. When the user presses the button 108, the letter "C" on the display 110 flashes and indicates that the transmitter 106 is selecting a channel thereby selecting an electrical stimulation unit to control with. For example shown in FIG. 3, a number "3" displayed by the letter "C" on the display 110 indicates a communication connection to the number 3 electrical stimulation unit. Pressing the button 108 again changes the channel on which the transmitter 106 operates and thus changes the electrical stimulation unit the transmitter 106 controls, and changes the number displayed on the display 110.

As shown in FIGS. 4-7, an electrode pad 107 having a pair of electrodes 142 is provided. An electrode pad 107 is preferably releasably connected with each electrical stimulation unit to apply a time-varying electric potential to the electrodes 142 to provide an electrical stimulation to tissue in electrical contact with the electrodes. In some preferred embodiments, a processor (not shown) may be provided in the electrical stimulation units to apply time-varying electric potential to the electrodes. The electrode pads 107 preferably have a pair of male metal snaps 114 for attaching to a pair of female metal snaps 115 on the electrical stimulation units. The metal snaps can alternatively be some other type or design of fastener for releasably engaging and electrically connecting the electrode pad 107 to the electrical stimulation unit.

The electrode pad 107 preferably includes a flexible substrate so that it can be easily applied on a body surface, for example, ankles, knees, wrists, shoulders, neck, etc. In other embodiments, the electrodes can also be carried on an article of clothing (e.g., accessories as gloves, socks, slippers, hats, etc.). The article of clothing preferably includes a pair of fasteners for removably attaching and electrically connecting with the electrical stimulation unit, forming an electronic circuit to apply an electrical stimulation to tissue in electrical contact with the electrodes.

At least some of the electrical stimulation units have at least two operating modes, each of which applies a time-varying electrical potential to the electrodes in a different pattern. FIGS. 8-19 illustrate some exemplary waveforms for four exemplary operating modes. Of course fewer or additional, or different operating modes having different pulse frequencies, pulse-widths, treatment pattern repetition cycles and amplitudes, can be provided. Below is a table summarizing the four example operating modes:

TABLE 1

Parameters for Four Modes Testing With a Load of 1KΩ

| | Pulse frequency (Hz) | Pulse-width (μs) | Treatment pattern repetition cycle(s) | Amplitude (V) |
|---|---|---|---|---|
| Mode 1 (FIGS. 8-9) | 52 | 100 | 4.5 | 60 |
| Mode 2 (FIGS. 10-12) | 11 | 100 | 4.5 | 75 |
| Mode 3 (FIGS. 13-14) | 1.2 | 100 | continuous | 75 |
| Mode 4 (FIGS. 15-19) | | | | |
| 1$^{st}$ Stage: | 1.9-8.3 | 100 | | 75 |
| 2$^{nd}$ Stage: | 60 | 100 | 90 (total) | 58 |
| 3$^{rd}$ Stage: | 1-11.5 | 100 | | 75 |
| 4$^{th}$ Stage: | 53.5 | 100 | | 60 |

The transmitter 106 preferably further includes a mode selector for selecting an operating mode for each electrical stimulation unit. The mode selector is preferably a single remote control button 112 that can be used to remotely, wirelessly transmit operating instructions of a user selected operating mode to the selected one of the plurality of wireless electrical stimulation units. The unit selector button 108 preferably has a letter "M" on it, indicating to the user that the button controls the mode. A user can select different operating modes by pressing the button 112, which cycles through the available modes. A user can select different wireless electrical stimulation unit by pressing the button 108, which can cycle through the available channels. In an alternative embodiment, pressing the button 112 switches the transmitter to the operating mode, and the mode can be changed by pressing increase and decrease buttons 120 and 122, described in more detail below.

The transmitter 106 can further include a display 116 for indicating which of the operating modes has been selected. When the user presses the mode selector 112, the letter "M" on the display 116 flashes and indicates that the transmitter 106 is selecting an operating mode for a selected electrical stimulation unit. For example shown in FIG. 3, a number "3" displayed adjacent the letter "M" on the display 110 indicates an operating mode 3 is selected for the selected electrical stimulation unit. Pressing the mode selector 112 can change the number displayed and thereby change the operating modes of the selected electrical stimulation unit to be controlled with. Alternatively, the mode selector button 112 can be pressed to enter the mode selection mode, and then the increase and decrease buttons 120 and 122 can be operated to select the desired mode.

Figure 7:
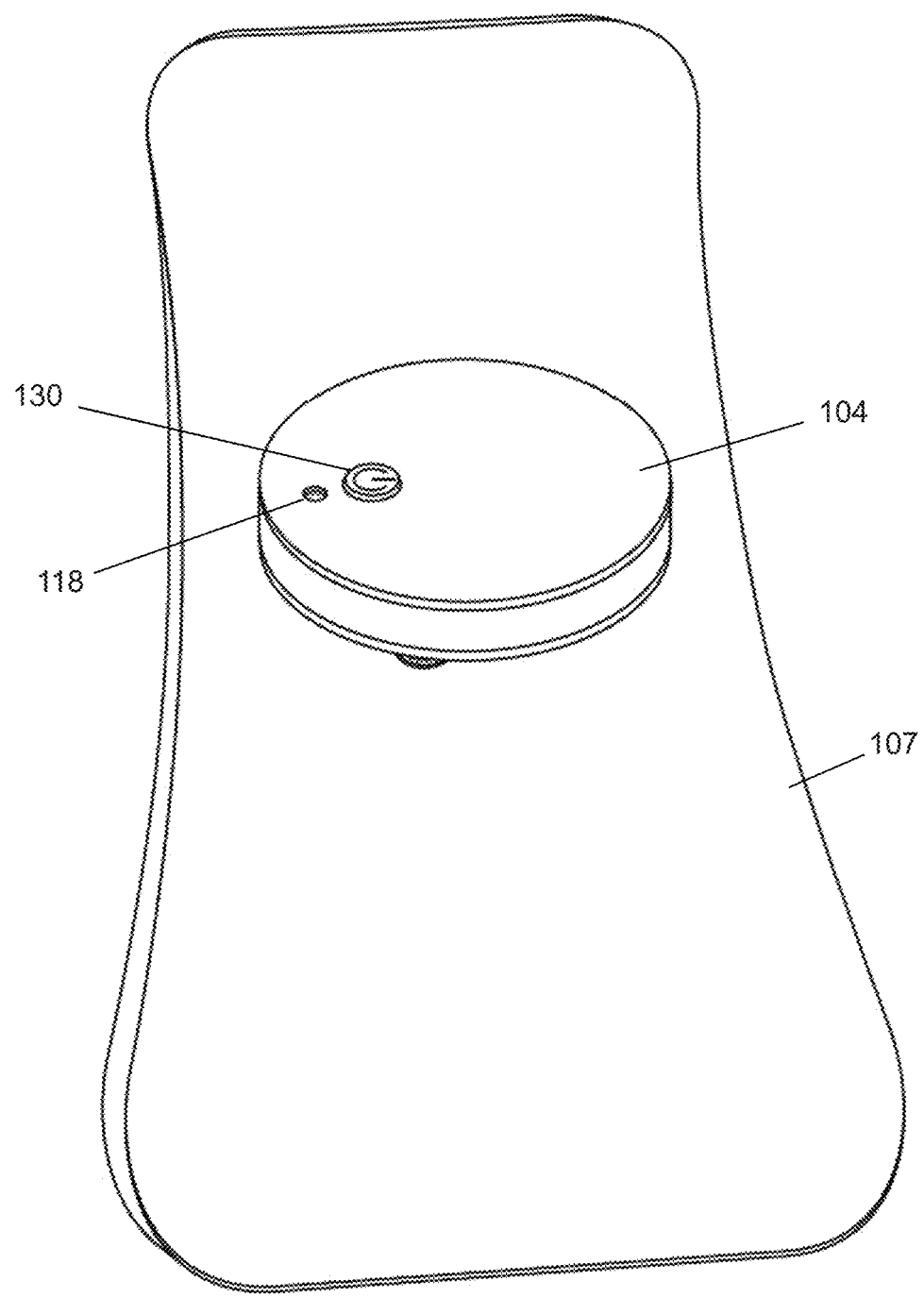
Figure 8:
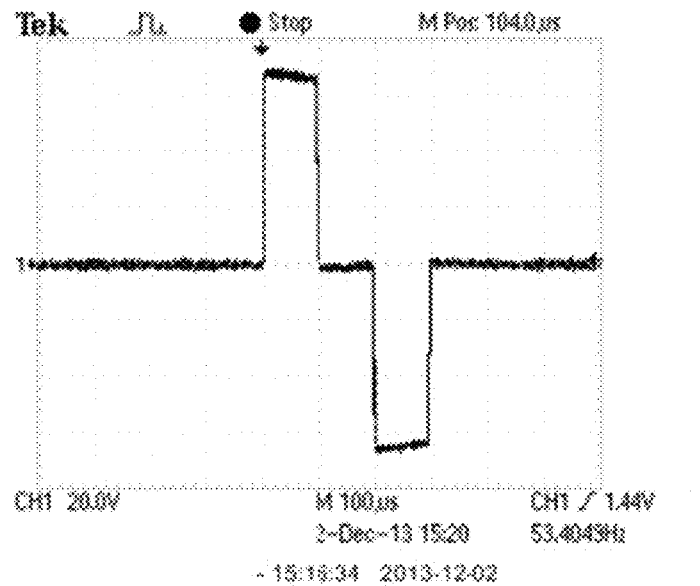
FIGS. 8 and 9 illustrate exemplary waveforms for an operating mode 1.
Figure 9:
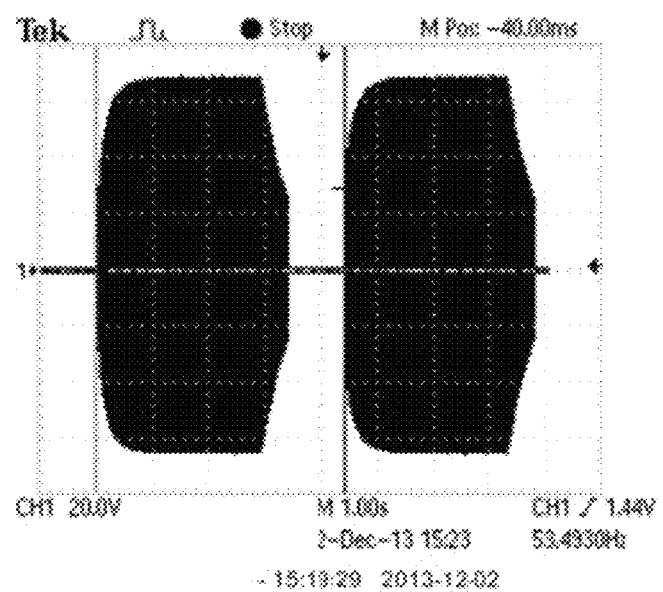
Figure 10:
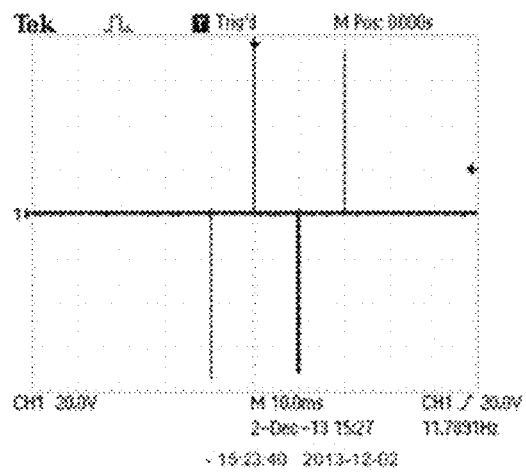
FIGS. 10-12 illustrate exemplary waveforms for an operating mode 2.
Figure 11:
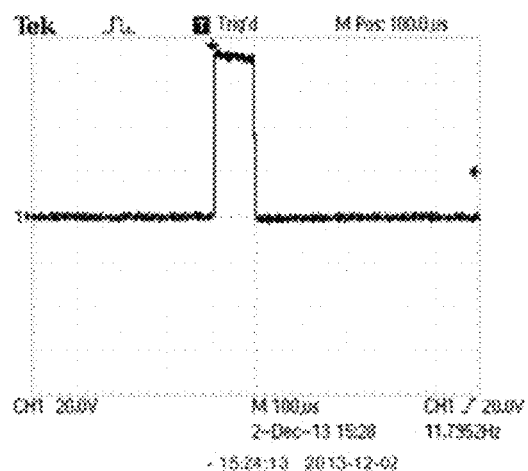
Figure 12:
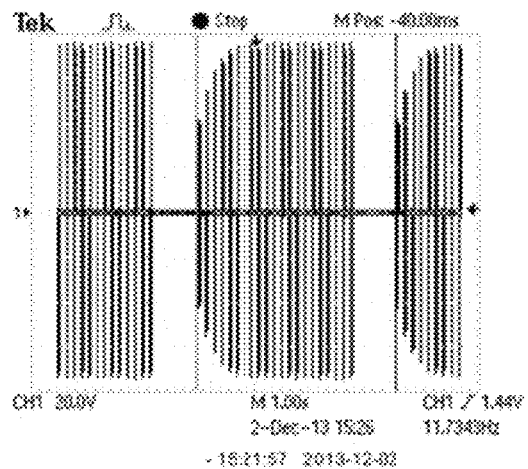
Figure 13:
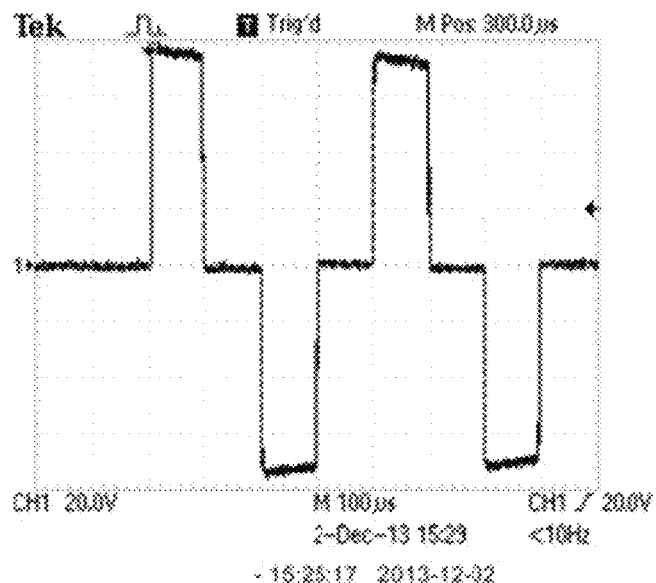
FIGS. 13 and 14 illustrate exemplary waveforms for an operating mode 3.
Figure 14:
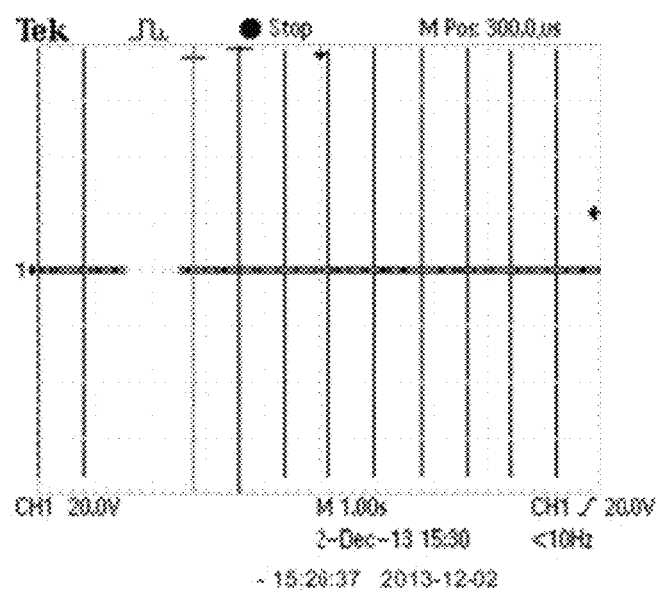
Figure 15:
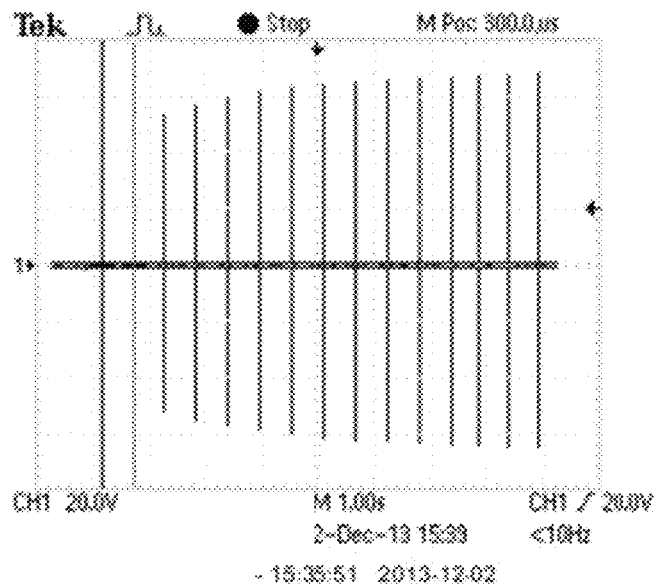
FIGS. 15-19 illustrate exemplary waveforms for an operating mode 4.
Figure 16:
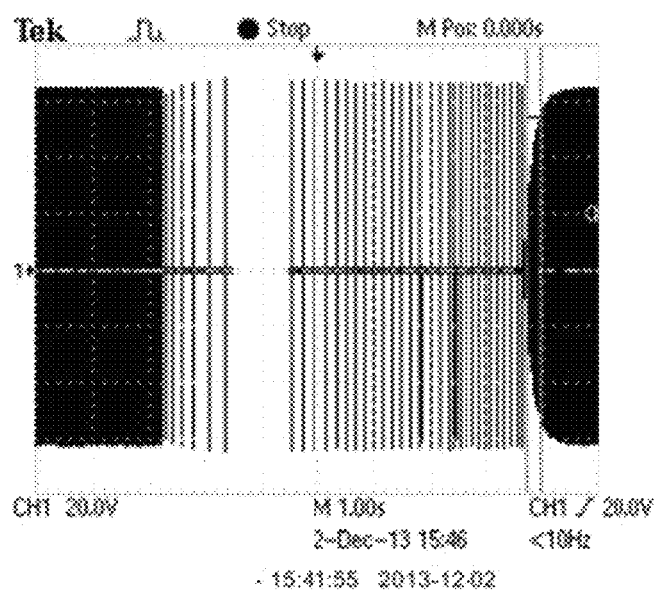
Figure 17:
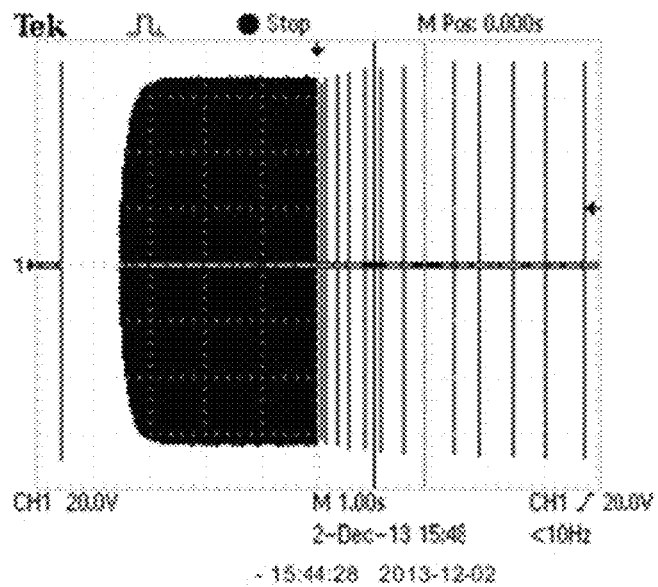
Figure 18:
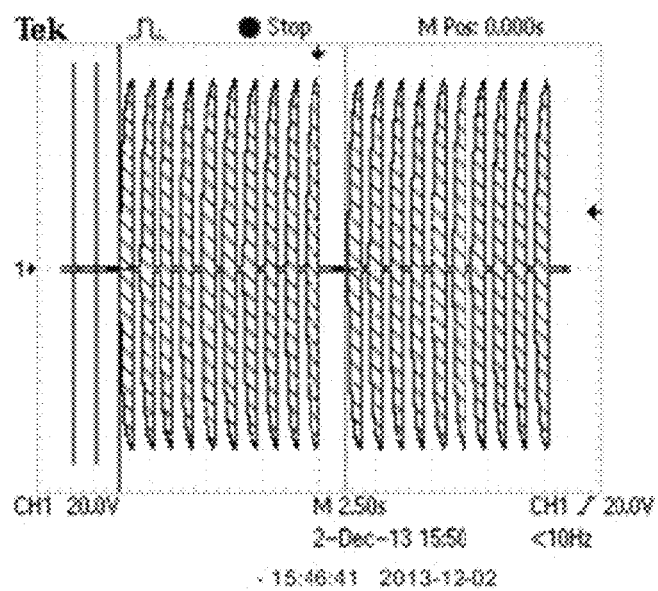
Figure 19:
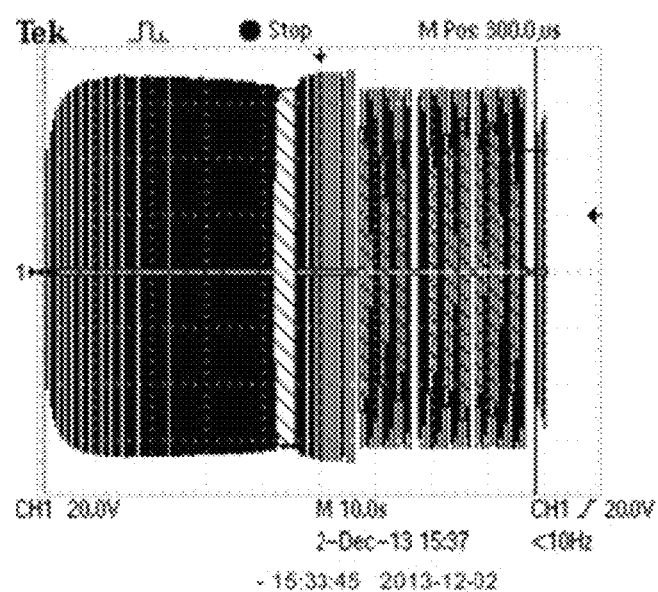

As shown in FIG. 7, at least some of the electrical stimulation units preferably include a working status indicator 118. The working status indicator 118 is "on" when the electrical stimulation unit is powered on. When an electrical stimulation unit 102, 104 is selected to be controlled, the working status indicator 118 of this selected electrical stimulation unit 102, 104 flashes or blinks in response to the operating instructions transmitted from the transmitter 106.

At least some of the electrical stimulation units are capable of operating at least two intensities. As shown in FIG. 3, the transmitter 106 includes an intensity selector for selecting different intensities. In the preferred embodiment shown in FIGS. 1-3, the intensity selector consists of an increase button 120 and a decrease button 122 for increasing and decreasing the operating intensity for the electrical stimulation unit to be controlled with. The increase button 120 and decrease button 122 are remote control buttons that remotely, wirelessly transmits operating instructions of a user selected intensity to a selected one of the plurality of wireless electrical stimulation units. The increase and decrease buttons 120 and 122 preferably have "+" and "−" signs respectively, to indicate their function to the user. A user can adjust the operating intensity by pressing the buttons 120 and 122 to a level the user desires.

As shown in FIG. 3, the transmitter 106 can further include a display 124 for indicating the level of the operating intensity that has been selected. When the user presses either the increase button 120 or the decrease button 122, the word "intensity" on the display 124 flashes and indicates that the transmitter 106 is selecting an operating intensity for the selected electrical stimulation unit. The display 124 preferably shows a number of bars along the circumferential edge of the display indicating the level of the intensity.

Figure 20:
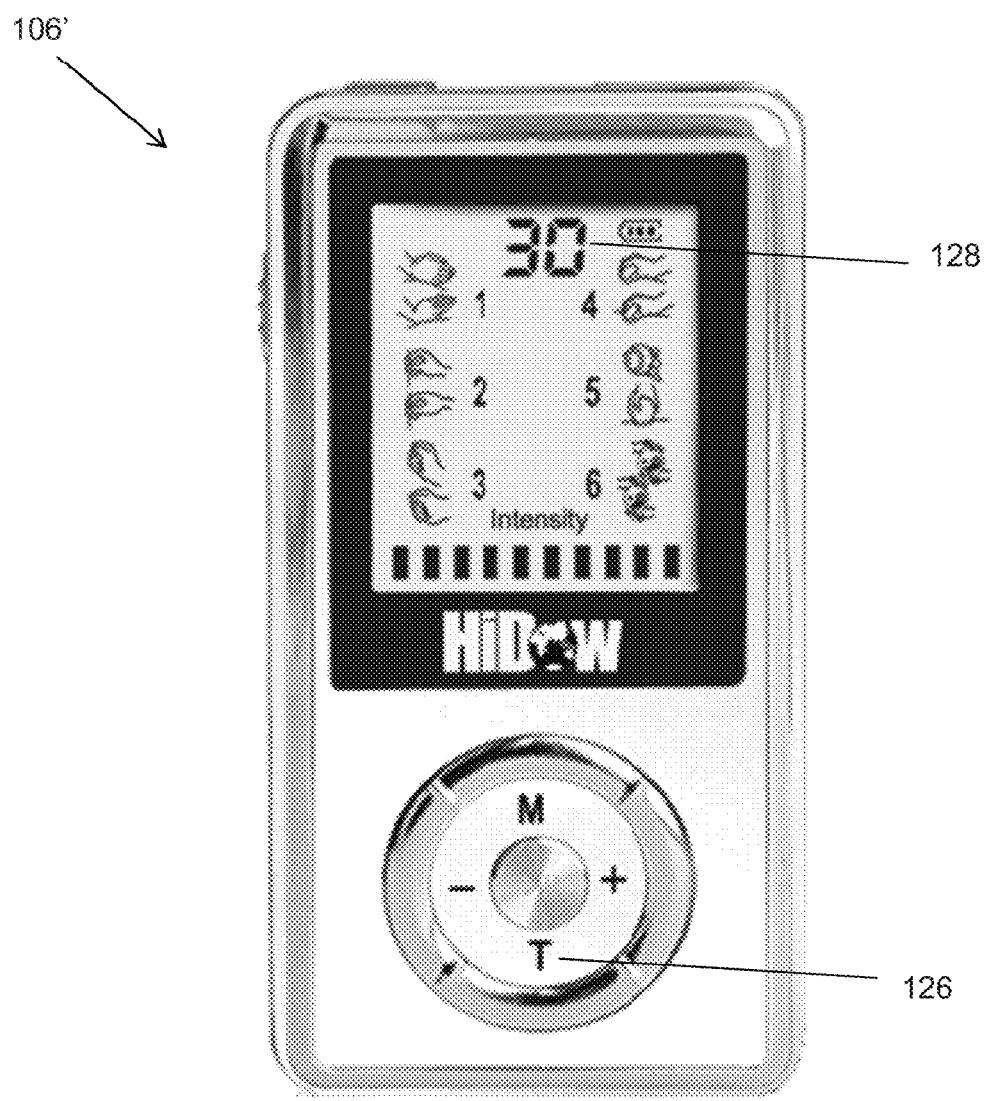
FIG. 20 is a front elevation view of another transmitter having a time selector button.

In an alternative embodiment shown in FIG. 20, the transmitter 106' preferably includes a time selector 126 for selecting a preferred operating time period for at least some of the electrical stimulation units. The time selector 126 is a single remote control button that remotely, wirelessly transmits operating instructions of a user selected operating time period/duration to a selected electrical stimulation unit. The time selector button 126 preferably has a letter "T" on it. A user can select different operating time period by continuing to press the button 126.

As shown in FIG. 20, the transmitter 106' further can include a display 128 for indicating the operating time period selected. When the user presses the time selector button 126, the number on the digital display 128 changes and indicates the operating time (preferably in minutes) being selected for a selected electrical stimulation unit to control with. The display 124 is preferably a digital display showing the number of minutes selected by the user.

In some embodiments, at least some of the electrical stimulation units turn off when communication with the transmitter 106 is interrupted. In some preferred embodiments, at least some of the electrical stimulation unit turns off a predetermined time after communication with the transmitter is interrupted. The predetermined time, for example, can be one quarter hour, one half an hour, or an hour. The communication may be interrupted due to a long distance between the electrical stimulation unit and the transmitter. For example, wireless communication technologies typically have a range of about 15 meters outdoors and about 10 meters indoors. The communication may alternatively be interrupted because the transmitter is turned off, or runs out of power. Accordingly, the user can turn off the transmitter to save battery, while the electrical stimulation units can continue operating at the preselected intensity and mode for the predetermined time. This feature may help the user stay safer when using the wireless electrical stimulation system.

In some embodiments, at least some of the electrical stimulation units preferably include a power switch 130 as shown in FIG. 7. The working status indicator 118 is on/off when the power switch is pressed on/off respectively.

Figure 21:
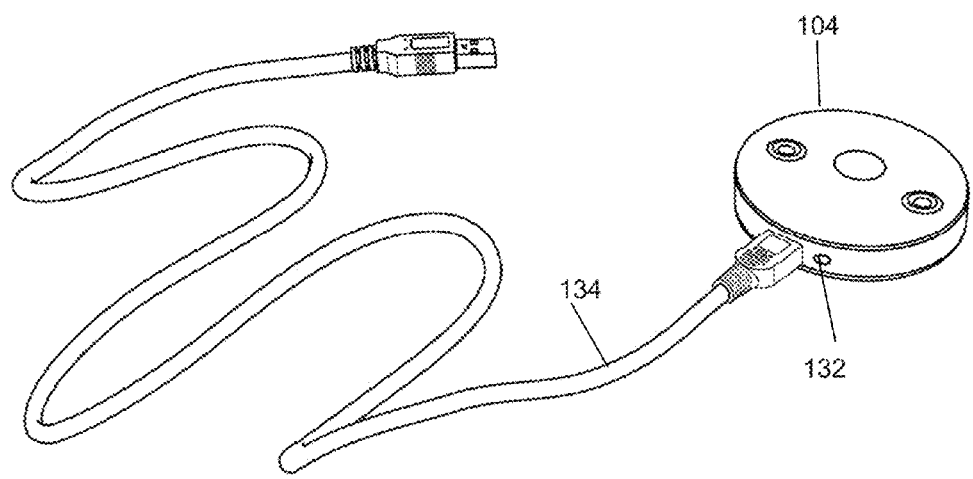
FIG. 21 is a perspective view of an electrode substrate of the wireless electrical stimulation system.
Figure 22:
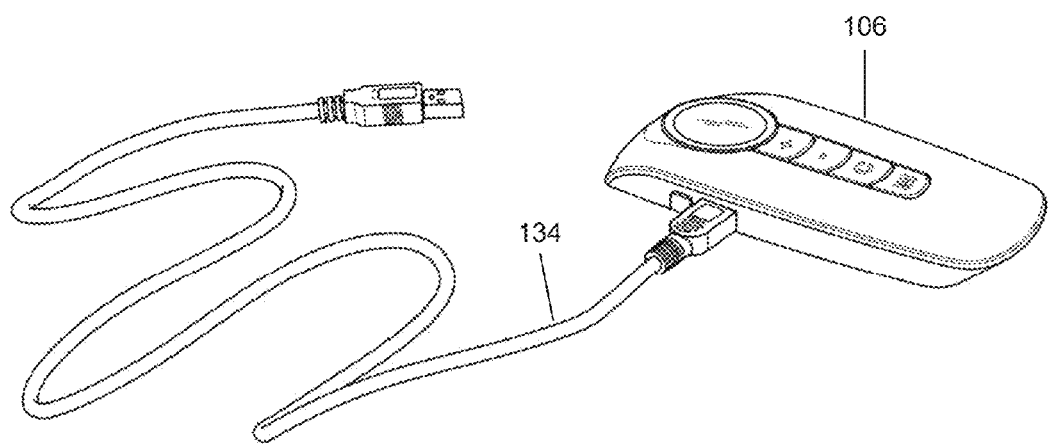
FIG. 22 is a receiver connected with the charging cable of the wireless electrical stimulation system.
Figure 23:
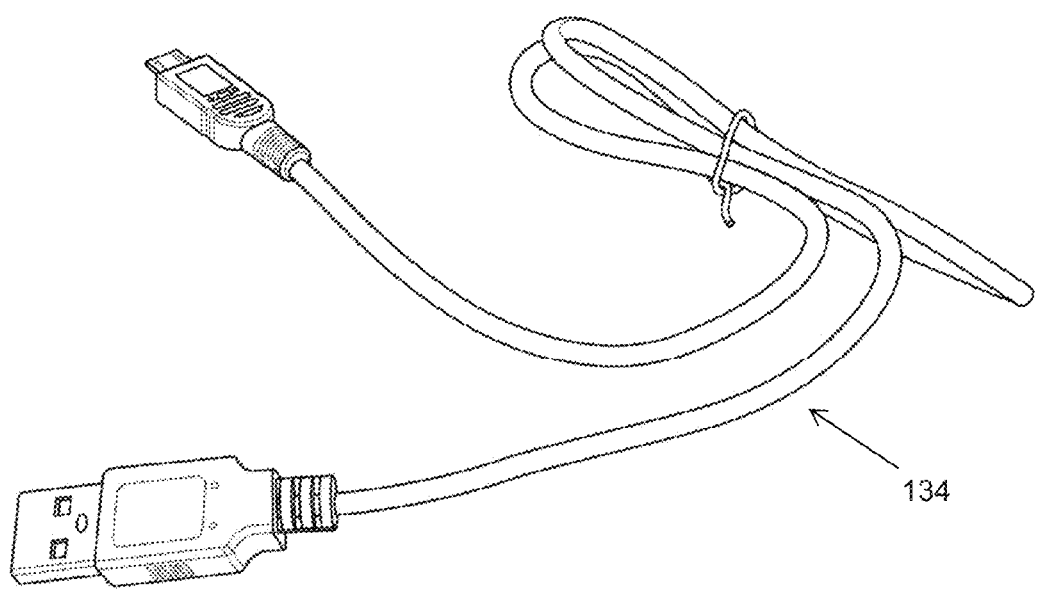
FIG. 23 is a charging cable of the wireless electrical stimulation system.
Figure 24:
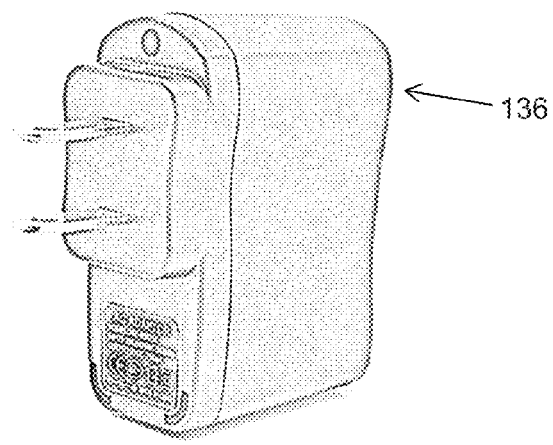
FIG. 24 is the transmitter connected with the charging cable.

Additionally, the transmitter and each electrical stimulation unit preferably include their own internal power supply (not shown). The internal power supply is preferably a rechargeable battery, or other suitable energy storage device. Each electrical stimulation unit preferably includes a charging indicator 132 as shown in FIG. 21. The charging indicator 132 is on when the electrical stimulation unit 104 is charging, and turns off when the electrical stimulation unit 104 is either disconnected form the charging source or is fully charged. Each electrical stimulation unit is preferably charged using a USB connector 134 connecting to an AC adapter 136. As shown in FIGS. 22-24, the USB connector 134 and the AC adapter 136 can also be used to charge a rechargeable battery in the transmitter 106. The transmitter 106 preferably includes a battery display 138 indicates the state of charge and/or charging status.

Figure 25:
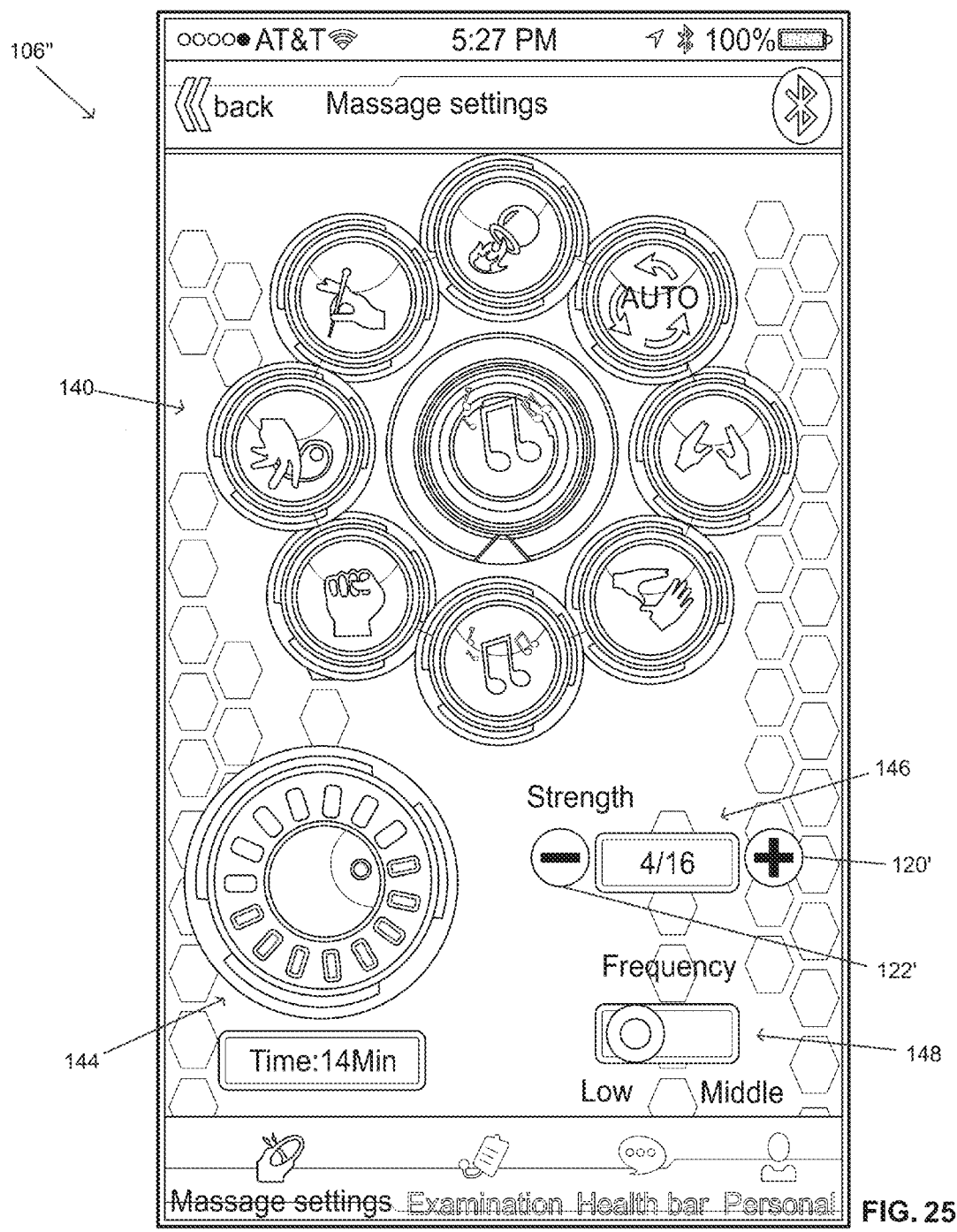
FIG. 25 is a smart phone having an application running as a transmitter of the wireless electrical stimulation system.

Alternatively, the transmitter 106" can be a smart phone running an application as shown in FIG. 25. The smart phone applications have different control buttons for the user to tap on to select the operating modes, operating time period, channels, intensity, massage strength and frequency, etc. For example shown in FIG. 25, the smart phone application can have a mode selector 140 for selecting an operating mode for at least some of the electrical stimulation units. The mode selector 140 preferably includes a group of buttons indicating different operating modes to choose from. The smart phone application preferably includes a time selector 144 for selecting/displaying a preferred operating time period for at least some of the electrical stimulation units. The time selector 144 preferably includes a virtual dial timer. A user can select a preferred operating time period by dialing the virtual dial timer of the time selector 144. The smart phone application further preferably includes an intensity selector 146 and a frequency selector 148 for selecting a preferred operating intensity and a preferred operating frequency respectively. The intensity selector 146 preferably includes an increasing button 120' and a decreasing button 122'. A user can adjust the operating intensity by pressing the buttons 120' and 122' to a level the user desires. The frequency selector 148 preferably includes a virtual slider control. A user can adjust the operating frequency by sliding the virtual slider control of the frequency selector 148 to a frequency the user desires.

In some embodiments, the transmitter wirelessly communicates with the electrical stimulation units via RF protocol operating in the 2.4 GHz band. For example, Bluetooth or Wifi technologies may be used.

Figure 26:
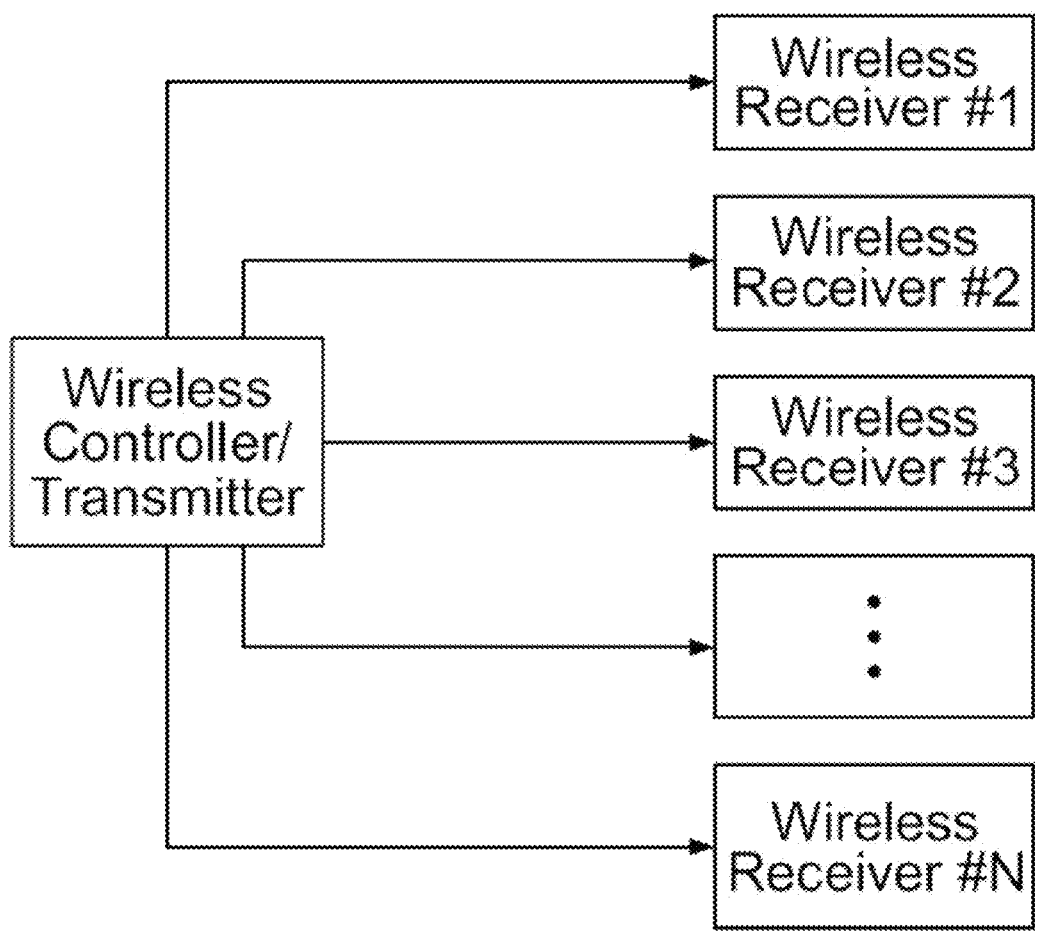
FIG. 26 is a schematic illustration of the wireless electrical stimulation system according to the present disclosure.

As shown in FIG. 26, one transmitter having a master RF transceiver chip can wirelessly control multiple electrical stimulation units having slave RF transceiver chips as receivers through 2.4 GHz wireless connections.

Figure 27:
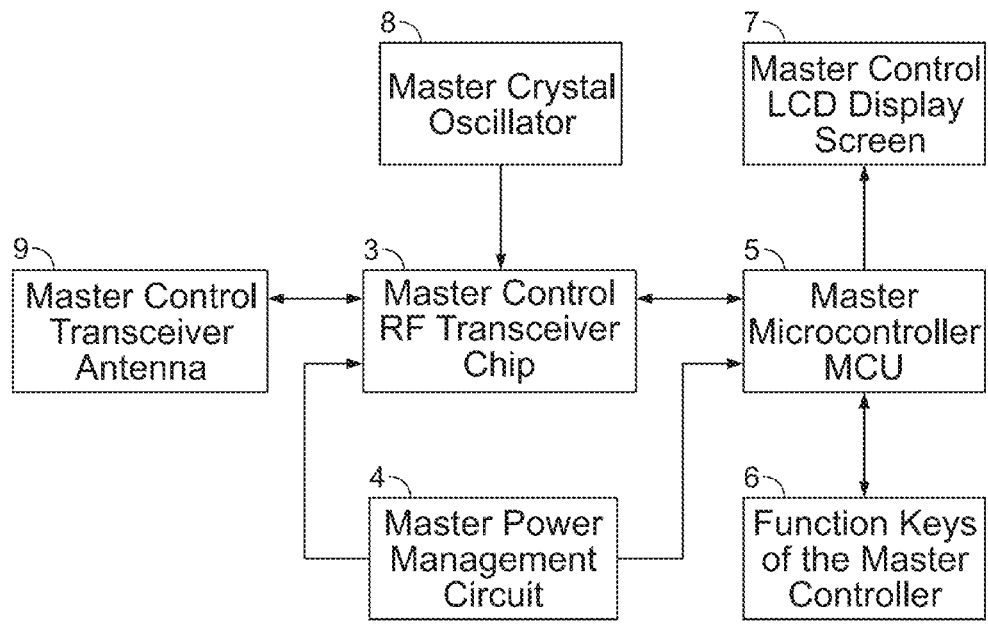
FIG. 27 is a schematic illustration of the transmitter of the wireless electrical stimulation system.

FIG. 27 is a schematic illustration of the transmitter of the wireless electrical stimulation system. The transmitter generally includes the master RF transceiver chip (3) with its input and output connected to a master transceiver antenna (9) and a master microcontroller (5). All the function keys of the master controller (6) are connected to the inputs of the master microcontroller (5). The master control LCD display screen (7) is connected to the output of master microcontroller (5). The input of the master RF transceiver chip (3) may also be connected to an output of a master crystal oscillator (8). A master power management circuit (4) generally supplies the electrical power to the master RF transceiver chip (3) and the master microcontroller (5). The master controller function keys (6) preferably include a channel selector "C", a mode selector "M", a time selector "T", an intensity increaser "+", and an intensity decreaser "−", etc.

Figure 28:
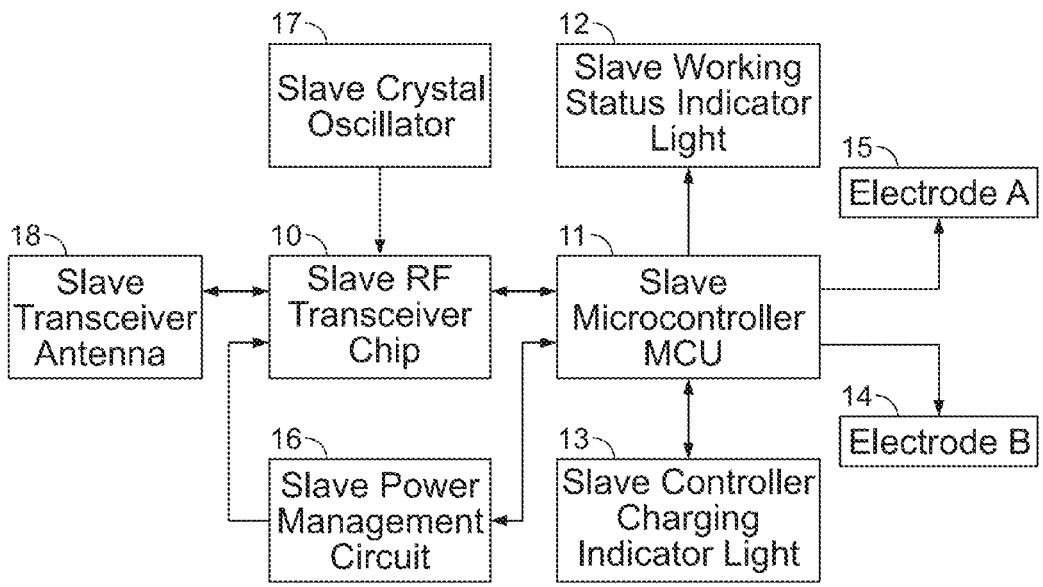
FIG. 28 is a schematic illustration of the receiver/electrical stimulation unit of the wireless electrical stimulation system.

FIG. 28 is a schematic illustration of the receiver/electrical stimulation unit of the wireless electrical stimulation system. The receiver/electrical stimulation unit generally includes a slave RF transceiver chip (10) with its input and output connected to a slave transceiver antenna (18) and a slave microcontroller (11). A slave working status indicator light (12) and a slave controller charging indicator light (13) are connected to the input and output of the slave microcontroller (11). A power switch is connected to the input and output of the slave microcontroller (11). An electrode A (15) and an electrode B (14) are connected to the outputs of the slave microcontroller (12). The input of the slave RF transceiver chip (10) is connected to an output of a slave crystal oscillator (17). A slave power management circuit (16) generally supplies the electrical power to the slave RF transceiver chip (10) and the slave microcontroller (11). The slave microcontroller may also control a slave working status indicator light (12) and a slave charging indicator light.

The wireless operation of a plurality of electrical stimulation units is implemented with the communication between the master RF transceiver chip (3) of the wireless transmitter (1) and the wireless slave RF transceiver chip (10) of the wireless receiver (2).

The master and slave RF transceiver chip (3), (10) is a highly integrated 2.4 GHz wireless transceiver chip. The master and slave microcontrollers (5) and (11) communicate with each other by using a transmit-receive FIFO register on the chip to store the data, and then transfer at a maximum 2 Mbps rate in the air to accomplish the wireless control.

The slave RF transceiver chip (10) is preferably a highly integrated 2.4 GHz RF transceiver chip. The slave RF transceiver chip (10) receives a data packet from the transmitter. The data packet is preferably an 8-bit unsigned data packet and is preferably stored in a First-In-First-Out (FIFO) register. The slave RF transceiver chip (10) then sends an Acknowledgement (ACK) signal to the transmitter to notify the transmitter that the data packet has been safely received. The maximum data transfer rate is preferably 2 Mbps. The buffer of the FIFO register is cleared after a communication is finished and the register is ready for the next communication.

The transmitter of the wireless electrical stimulation system preferably matches the code sent by each electrical stimulation units with a predetermined code before connecting with one of the plurality of the electrical stimulation units to further control the operation of each electrical stimulation unit. The transmitter preferably communicates with different electrical stimulation units on different channels at different frequencies. Alternatively the communication could be on the same channel at the same frequency, with each message encoded for a particular electrical stimulation unit. Of course in some applications it may be desirable that a transmitter simultaneously control multiple electrical stimulation units, and thus in some embodiments at least some of the electrical stimulation units operate on the same channel or frequency, or are responsive to the same encoded signals.

Further, in order to allow more convenient control, the transmitter of the wireless electrical stimulation system preferably consolidates all the necessary selector displays on one single LCD screen. The LCD screen also displays the working status of the electrical stimulation units, such as the operating modes, the operating intensities, the operation time periods, etc., and the status of the transmitter, such as the state of the charge and the receivers currently being controlled, etc.

Exemplary embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail. In addition, advantages and improvements that may be achieved with one or more exemplary embodiments of the present disclosure are provided for purpose of illustration only and do not limit the scope of the present disclosure, as exemplary embodiments disclosed herein may provide all or none of the above mentioned advantages and improvements and still fall within the scope of the present disclosure.

Specific dimensions, specific materials, and/or specific shapes disclosed herein are examples in nature and do not limit the scope of the present disclosure. The disclosure herein of particular values and particular ranges of values for given parameters are not exclusive of other values and ranges of values that may be useful in one or more of the examples disclosed herein. Moreover, it is envisioned that any two particular values for a specific parameter stated herein may define the endpoints of a range of values that may be suitable for the given parameter (i.e., the disclosure of a first value and a second value for a given parameter can be interpreted as disclosing that any value between the first and second values could also be employed for the given parameter). For example, if Parameter X is exemplified herein to have value A and also exemplified to have value Z, it is envisioned that parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

The terminology used herein is for the purpose of describing particular exemplary embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

The term "about" when applied to values indicates that the calculation or the measurement allows some slight imprecision in the value (with some approach to exactness in the value; approximately or reasonably close to the value; nearly). If, for some reason, the imprecision provided by "about" is not otherwise understood in the art with this ordinary meaning, then "about" as used herein indicates at least variations that may arise from ordinary methods of measuring or using such parameters. For example, the terms "generally," "about," and "substantially," may be used herein to mean within manufacturing tolerances. Or for example, the term "about" as used herein when modifying a quantity of an ingredient or reactant of the invention or employed refers to variation in the numerical quantity that can happen through typical measuring and handling procedures used, for example, when making concentrates or solutions in the real world through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about," the claims include equivalents to the quantities.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A wireless electrical stimulation system comprising:
    at least two electrical stimulation units, each electrical stimulation unit having electrodes connected to the electrical stimulation unit and configured to deliver electrical pulses to muscle groups or nerve areas adjacent a body surface to which the electrodes are applied, wherein the electrodes are configured to be applied externally to the body; and
    a transmitter for remotely, wirelessly controlling each of the electrical stimulation units by transmitting operating instructions corresponding to a selected one of a plurality of operating modes to each of the electrical stimulation units on separate channels at different frequencies using a single remote control and matching a code sent by each of the electrical stimulation units with a predetermined code before sending the operating instructions to selectively apply a time-varying electric potential to the electrodes to provide an electrical stimulation to the muscle groups or the nerve areas through the body surface in electrical contact with the electrodes, wherein the operating instructions corresponding to the selected one of the plurality of operating modes for a plurality of treatment patterns to the muscle groups and the nerve areas are transmitted on the separate channels by the transmitter to the at least two electrical stimulation units, and include at least one of a plurality of pulse frequencies, a plurality of pulse-widths, a plurality of treatment pattern repetition cycles, a plurality of amplitudes, a plurality of intensities, and a plurality of time periods of operation, wherein the transmitter includes a unit selector configured to allow a user to select one of the at least two electrical stimulation units to control with the transmitter.

2. The wireless electrical stimulation system according to claim 1, wherein the electrodes are releasably connected to the electrical stimulation unit.

3. The wireless electrical stimulation system according to claim 1, wherein the transmitter includes a display for indicating which of the electrical stimulation units has been selected.

4. The wireless electrical stimulation system according to claim 1, wherein each electrical stimulation unit has at least two operating modes, each of which applies a time-varying electrical potential to the electrodes in a different pattern, and wherein the transmitter has a mode selector for selecting one of the at least two operating modes for each electrical stimulation unit.

5. The wireless electrical stimulation system according to claim 4, wherein the transmitter includes a display for indicating which of the operating modes has been selected.

6. The wireless electrical stimulation system according to claim 1, wherein each electrical stimulation unit is capable of operating at at least two intensities, and wherein the transmitter has an intensity selector for selecting one of the at least two intensities of operation for each electrical stimulation unit.

7. The wireless electrical stimulation system according to claim 6, wherein the intensity selector comprises an increase control and a decrease control.

8. The wireless electrical stimulation system according to claim 6, wherein the transmitter includes a display for indicating the intensity that has been selected.

9. The wireless electrical stimulation system according to claim 1, wherein each electrical stimulation unit is capable of operating for a selectable time period, and wherein the transmitter has a time selector for selecting the time period of operation for each electrical stimulation unit.

10. The wireless electrical stimulation system according to claim 1, wherein the transmitter is a smart phone running an application.

11. The wireless electrical stimulation system according to claim 1, wherein the electrical stimulation unit is carried on a flexible substrate to be applied on the body surface.

12. The wireless electrical stimulation system according to claim 1, wherein the electrical stimulation unit is carried on an article of clothing.

13. The wireless electrical stimulation system according to claim 1 further comprising a USB connector configured to operatively charge the transmitter and/or a receiver.

14. The wireless electrical stimulation system according to claim 13 further comprising an AC adapter configured to operatively charge the transmitter and/or the receiver.

15. A wireless electrical stimulation system comprising:
at least two electrical stimulation units, each electrical stimulation unit having electrodes connected to the electrical stimulation unit and configured to deliver electrical pulses to muscle groups or nerve areas adjacent a body surface to which the electrodes are applied, wherein the electrodes are configured to be applied externally to the body and a processor for applying a time-varying electric potential to the electrodes to provide an electrical stimulation to the muscle groups or the nerve areas through the body surface in electrical contact with the electrodes; and
a transmitter for remotely, wirelessly controlling each of the electrical stimulation units, the transmitter comprising a unit selector configured to allow a user to select one of the at least two electrical stimulation units by selecting one of the at least two channels at different frequencies and matching a code sent by each of the electrical stimulation units with a predetermined code before sending operating instructions corresponding to a selected one of a plurality of operating modes to control with the transmitter on separate channels at different frequencies, and a display for indicating which of the electrical stimulation units has been selected, wherein the operating instructions corresponding to the selected one of the plurality of operating modes for a plurality of treatment patterns to the muscle groups and the nerve areas are transmitted on the separate channels by the transmitter to the at least two electrical stimulation units, and include at least one of a plurality of pulse frequencies, a plurality of pulse-widths, a plurality of treatment pattern repetition cycles, a plurality of amplitudes, a plurality of intensities, and a plurality of time periods of operation.

16. The wireless electrical stimulation system according to claim 15, wherein the electrodes are releasably connected to the electrical stimulation unit.

17. The wireless electrical stimulation system according to claim 15, wherein each electrical stimulation unit has at least two operating modes each of which applies a time-varying electrical potential to the electrodes in a different pattern, and wherein the transmitter has a mode selector for selecting one of the at least two operating modes for each electrical stimulation unit, and a display for indicating which of the operating modes has been selected for the electrical stimulation unit being controlled.

18. The wireless electrical stimulation system according to claim 17, wherein each electrical stimulation unit is capable of operating at at least two intensities, and wherein the transmitter has an intensity selector for selecting one of the at least two intensities of operation for each electrical stimulation unit, and a display for indicating the intensity that has been selected for the electrical stimulation unit being controlled.

19. The wireless electrical stimulation system according to claim 15 wherein the transmitter communicates with the electrical stimulation units via a radio frequency (RF) protocol.

20. The wireless electrical stimulation system according to claim 15 wherein each electrical stimulation unit turns off when communication with the transmitter is interrupted.

21. The wireless electrical stimulation system according to claim 15 wherein each electrical stimulation unit turns off a predetermined time after communication with the transmitter is interrupted.

22. The wireless electrical stimulation system according to claim 15 wherein each electrical stimulation unit has a power switch, and an indicator that indicates when the power is on.

23. The wireless electrical stimulation system according to claim 22 wherein each electrical stimulation unit has an internal power supply, and further comprises an indicator for indicating a status of the internal power supply.

* * * * *